United States Patent
Florio et al.

[11] Patent Number: 5,913,253
[45] Date of Patent: *Jun. 15, 1999

[54] PROCESS FOR EVALUATING THE ENVIRONMENTAL IMPACT OF COMPONENTS OF LUBRICATING OILS

[75] Inventors: Salvatore Florio, Barano D'ischia; Massimo Manni, San Donato Milanese; Giovanni Livraghi, Maleo, all of Italy

[73] Assignee: Euron S.p.A., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/866,391

[22] Filed: May 30, 1997

[30] Foreign Application Priority Data

May 31, 1996 [IT] Italy .................................. MI96A1110

[51] Int. Cl.$^6$ .................................................. G01M 15/00
[52] U.S. Cl. ............................................................ 73/865.6
[58] Field of Search ............................... 73/23.31, 23.32, 73/23.33, 865.6, 53.03, 116

[56] References Cited

FOREIGN PATENT DOCUMENTS 2 681 690   3/1993   France .

OTHER PUBLICATIONS

Database WPI, Week 7732, Derwent Publications Ltd., AN 77–57079Y & SU 531079, Feb. 11, 1977.
Michael Dowling, Exxon Chemical Co. Ltd., No. 922198, pp. 1–14, Oct. 19, 1992, "The Impact of Oil Formulation on Emissions from Diesel Engines".

*Primary Examiner*—Robert Raevis
*Attorney, Agent, or Firm*—Oblon, Spivak, McClelland, Maier & Neustadt, P.C.

[57] ABSTRACT

Process for determining the effect of lubricants and the relative components on exhaust emissions, specifically on the particulate, of an internal combustion engine which comprises:

(a) feeding, under almost constant flow rate conditions, the lubricant, or its components, to a single-orifice injector, through which the lubricant is sprayed into the intake air manifold of an engine; the flow rate of the lubricant is regulated to be from 2 to 8% of the flow rate of the fuel; the viscosity of the lubricant near the single-orifice injector being from 30 to 50 cSt;

(b) combustion of the lubricant and fuel with the consequent formation of exhaust gases;

(c) evaluation of the gases and of the particulate contained in the exhaust gases formed in step (b).

14 Claims, 1 Drawing Sheet

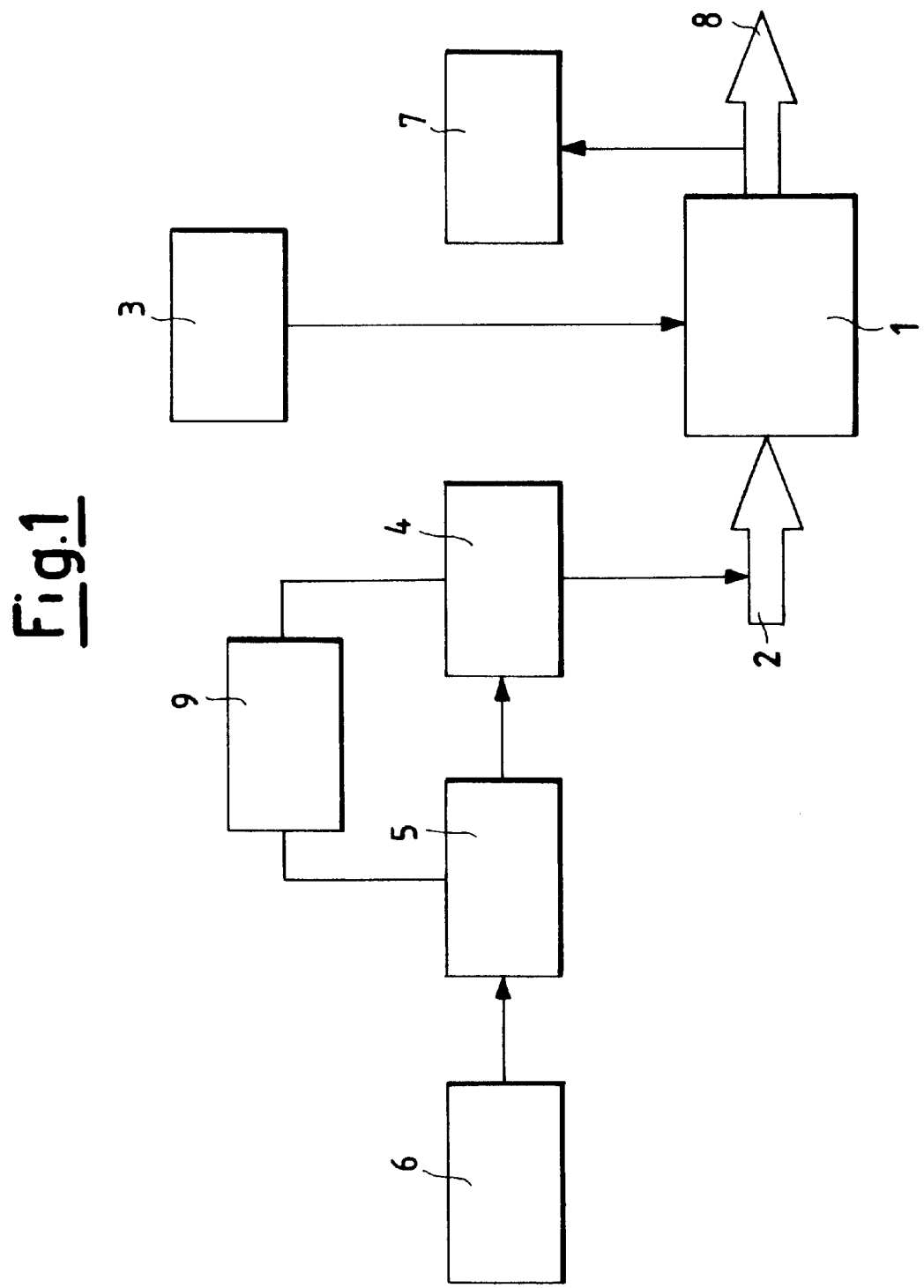

PROCESS FOR EVALUATING THE ENVIRONMENTAL IMPACT OF COMPONENTS OF LUBRICATING OILS

The present invention relates to a process for evaluating the influence of lubricants, and relative components, on the exhaust emissions of an internal combustion engine, particularly diesel engines.

It is known that the exhaust emissions of internal combustion engines are not only influenced by fuels but also by lubricants. There is therefore the problem of determining which lubricants are less polluting.

In the normal running of reciprocating engines, the various engine components obviously need lubrication. A part of the lubricant used for this purpose draws into the combustion chamber and burns together with the fuel, thus contributing to the emission of exhaust pollutants.

The more or less complete combustion of the lubricant and consequent contribution to the exhaust emissions depend on the chemical nature of the product (or components of the product).

To study the problem, it is useful to try and reproduce the actual phenomenum and appropriately amplify it.

In normal running, the oil arrives in the combustion chamber both through the cylinder/piston assembly and the valve zone. The first contribution can be magnified by eliminating or inverting, for example, the second piston ring; the second contribution can be more easily magnified by removing the rubber valve seals and increasing the clearance between the valve stem and guide. With these devices it is possible to amplify the oil-drawing towards the combustion chamber making it easier to study the lubricant combustion; it would be difficult however to establish the exact burnt quantity, change the lubricant in the oil sump for each product to be tested and evaluate the single components.

A more effective solution consists in simulating the oil-drawing into the chamber, by letting the test oil into the intake air manifold.

This solution was adopted by M. Dowling (S.A.E. No. 922198) who nebulized the oil into the intake air manifold of the engine. Dowling's method seemed rather coarse mainly with respect to defining the feeding flow rates, with the disadvantage of not being able to correctly distinguish the quantitative and qualitative contribution of the oil.

A partializing valve of the intake air was infact used for creating the necessary depression for spraying the oil but it reduced the flow rate of the air aspirated, with inevitable negative consequences on the volumetric efficiency of the engine.

A process has now been found for evaluating the effect of lubricants, and relative components, on the exhaust emissions of an internal combustion engine, particularly diesel, which overcomes the disadvantages described above.

In accordance with this, the present invention relates to a process for determining the effect of lubricants, and relative components, on the exhaust emissions, specifically on the particulate, of an internal combustion engine, particularly diesel, which comprises:

(a) feeding, under almost constant flow rate conditions, the lubricant, or its components, to a single-orifice injector, through which the lubricant is sprayed into the intake air manifold of an internal combustion engine fed with an appropriate fuel; the flow rate of the lubricant being regulated so that it is from 2 to 8%, preferably from 3 to 7%, even more preferably about 5%, of the flow rate of the fuel; the viscosity of the lubricant near the single-orifice injector being from 30 to 50 cSt, preferably from 30 to 50 cSt, even more preferably about 40 cSt;

(b) combustion of the lubricant and fuel with the consequent formation of exhaust gases;

(c) evaluation of the gaseous components and particulate contained in the exhaust gases formed in step (b).

The term particulate means the material contained in the exhaust gases as a solid or liquid finely subdivided, i.e. as a material which can be separated by filtration.

In the preferred embodiment the flow rate of the lubricant is regulated by a metering pump.

As not all lubricants, or their components, have the same viscosity, the necessary constancy of the spray (shape and dimensions of the droplets at the outlet of the injector) must be ensured by varying the temperature at which the lubricant is fed to the injector, in accordance with Walther's equation which correlates viscosity and temperature of fluids. More viscous products will be fed at higher temperatures, whereas less viscous products will be fed at lower temperatures. The temperature at which the lubricants, or relative components, are injected is such as to allow all lubricants to be tested to reach the injector essentially with a viscosity of between 30 and 50 cSt, preferably between 35 and 45 cSt, even more preferably about 40 cSt.

In a preferred embodiment, the metering pump, the line which connects the metering pump to the injector and the injector itself, must therefore be thermostat-regulated.

As far as analyzing the exhaust gases is concerned, the gaseous components are preferably analyzed by CO, HHC and $NO_x$ analyzers, with non-dispersive infra-red, flame ionization and chemiluminescence detectors respectively, whereas the particulate is evaluated by the weight increase of particular filters.

The process of the present invention enables lubricating oils, or relative components, having different physico-chemical characteristics to be reliably and repeatedly analyzed.

In fact the process of the present invention is carried out with negligible alterations of the engine running and without being affected by the different physico-chemical characteristics of the lubricant. This is possible due to the fact that the lubricants reach the injector with basically the same viscosity and flow rate, and also because the injector directs the lubricant spray onto the valve stem, thus reproducing the actual phenomenum.

The process of the present invention also has the advantage of requiring very reduced analysis times.

A further object of the present invention relates to an apparatus suitable for evaluating the impact on the exhaust emissions of an internal combustion engine, particularly a diesel engine, due to lubricants and relative components which, with reference to FIG. 1, comprises:

an internal combustion engine (1) to which an intake air manifold (2) and a fuel feeding line (3) are connected, a single-orifice injector (4) being connected to the intake air manifold, said injector feeding, at an almost constant flow rate, lubricating oil to the above; the above injector (4) being fed by lubricating oil by means of a pump (5) which sucks up the lubricant from a storage tank (6); suitable means (7) for analyzing the solid and gases contained in the exhaust gases (8) produced by the combustion in the engine.

In the preferred embodiment, the injector, the head of the metering pump, the tank-pump and pump-injector connection lines, are maintained at a constant temperature.

The means suitable for analyzing the particulate contained in the exhaust gases produced by combustion in the engine, possibly diluted with an inert gas, preferably air, are preferably filters.

The apparatus of the present invention is represented in FIG. 1, where (1) is the engine, (2) the intake air manifold, (3) the feeding line of the fuel, (4) the oil injector, (5) the oil metering pump, (6) the oil tank, (7) the exhaust gas sampler and analyzer, (8) the exhaust pipe, (9) the thermoregulator.

The following examples provide a better understanding of the present invention.

EXAMPLES

1) Test Procedure

The tank of the product to be tested is filled and the temperature to be reached by the thermoregulator is set, with the engine running under the test conditions selected in relation to the type of engine. The above temperature is selected on the basis of the viscosity curve of the product under examination with the aim of having a viscosity at the injector of about 40 cSt.

The flow rate of the metering pump is also regulated to obtain the established quantity in the 10 minutes test time (about 5% of the flow rate of fuel under those conditions) and the experiment involving a succession of various sampling, is started.

The first sampling takes place without injection of the lubricant to identify the reference values of the exhausts, whereas in the second sampling the metering pump is activated to measure the effects of the injection of the test product.

The test product under examination is fed into the intake air manifold from which it reaches the engine. At the end of the combustion, the exhaust gases are sampled and analyzed.

According to the European emission legislation (CEE 91/441 and 88/77), the exhaust gases reach the dilution tunnel where, after suitable mixing with air, they are sampled on a 90 mm teflon filter for the particulate and subsequently weighed with a high precision scale. The gaseous pollutants, on the other hand are sampled freshly on line, dehumidified and delivered to the CO, HHC and $NO_x$ analyzers, non-dispersive infra-red, flame ionization and chemiluminescence detectors respectively.

The whole experiment is repeated three times to be able to evaluate the repeatability and have valid results from a statistic point of view.

2) Application of the Test Method

The method described was applied using two single-cylinder diesel engines, the first a two-valve Ruggerini RW 120, the second a four-valve Hydra HSDI with a central injector.

The tests were carried out under high load conditions: 28 Nm at 2500 rpm for the Hydra; the same conditions at 2800 rpm for the Ruggerini.

To evaluate the efficiency of the method, two lubricating basestocks were first used, and considered as reference products for the potential emissions relating to their chemical nature: the first product, marked as Low Reference, is a product with a high content of aromatic hydrocarbons for which high particulate emissions were expected; the second, marked as High Reference, is an oxygenated product having a poor affinity with the fuel for which good behaviour with respect to particulate discharge was expected. Table 1 indicates some of the main characteristics of the reference products and the products subsequently evaluated. The above table also shows the kinematic viscosity (at 100° C. in cSt) of the products tested and the injection temperature.

It can be observed how the higher the viscosity the higher the injection temperature will be.

TABLE 1

| Product | Chemical nature/ origin | Aromatic Content | Kin. Vis. 100° C. cSt | Inj. T. ° C. |
|---|---|---|---|---|
| Low Ref | alkylbenzene | high | 17.5 | 65 |
| High Ref | synthetic | zero | 11 | 50 |
| A | synthetic | zero | 5.9 | 30 |
| B | synthetic | zero | 20 | 90 |
| C | synthetic | zero | 4.4 | 20 |
| D | hydrocracked | low | 6.6 | 40 |
| E | mineral | medium | 5.3 | 35 |

On both the engines, the reference products gave the expected effect proving to be very different from each other, as can be seen in table 2 below, which shows the particulate exhaust in g/kWh.

TABLE 2

| PRODUCT | RUGGERINI | HYDRA |
|---|---|---|
| Low Reference | 0.96 ± 0.11 | 1.70 ± 0.19 |
| High Reference | 0.53 ± 0.10 | 0.33 ± 0.04 |

Once the capacity of the method of the present invention to distinguish the reference products on different engines had been ascertained, the five products whose characteristics are shown in table 1, were examined.

To provide a comparison between the results obtained from the different products on the two engines, table 3 shows the demerits relating to the particulate emissions for each product tested, demerit 1 referring to the Low Reference product and 0 to the High Reference product. It can be seen how on both engines the demerit scale relating to the different products is well respected, thus proving the high capacity of the method to distinguish the products even on different engines.

TABLE 3

| PRODUCT | RUGGERINE | HYDRA |
|---|---|---|
| Low Reference | 1.00 | 1.00 |
| High Reference | 0.00 | 0.00 |
| A | 0.28 | 0.39 |
| B | 0.32 | 0.24 |
| C | 0.48 | 0.58 |
| D | 0.50 | 0.42 |
| E | 0.58 | 0.71 |

We claim:

1. A process for determining the effect of lubricants or relative components thereof on exhaust emissions, comprising gases and particulates, of an internal combustion engine, which process comprises:

a) feeding, under almost constant flow rate conditions, the lubricant or relative components thereof to a single-orifice injector, through which the lubricant or relative components thereof is sprayed into the intake air manifold of an internal combustion engine fed with an appropriate fuel; the flow rate of the lubricant being regulated so that it is from 2 to 8% of the flow rate of the fuel; the viscosity of the lubricant in the injector being from 30 to 50 cSt;

b) combusting the lubricant and fuel with the consequent formation of exhaust gases; and c) evaluating the gases and particulates contained in the exhaust gases formed in step b).

2. The process of claim 1, wherein the engine is a diesel engine.

3. The process of claim 1, wherein the flow rate of the lubricant is from 3 to 7% of the flow rate of the fuel.

4. The process of claim 3, wherein the flow rate of the lubricant is about 5% of the flow rate of the fuel.

5. The process of claim 1, wherein the viscosity of the lubricant near the single-orifice injector is from 35 to 45 cSt.

6. The process of claim 5, wherein the viscosity of the lubricant near the single-orifice injector is about 40 cSt.

7. The process of claim 1, wherein the flow rate of the lubricant is regulated by metering pump means, thereby obtaining said almost constant flow rate conditions.

8. The process of claim 7, wherein said metering pump means is regulated by a thermostat.

9. The process of claim 1, wherein said evaluating step c) is effected for gases by a CO analyzer using a non-dispersive infrared detector.

10. The process of claim 1, wherein said evaluating step c) is effected for gases by a HHC analyzer using a flame ionization detector.

11. The process of claim 1, wherein said evaluating step c) is effected for gases by a $NO_x$ analyzer using a chemiluminescence detector.

12. The process of claim 1, wherein said evaluating step c) is effected for particulates by weight increase of particulate filters.

13. An apparatus suitable for evaluating the impact of lubricants on exhaust emissions of an internal combustion engine, which comprises:

an internal combustion engine to which an intake air manifold and a fuel feeding line are connected, a single-orifice injector being connected to the intake air manifold, said injector sending, at an almost constant flow rate, lubricating oil to the above intake air manifold; the above single-orifice injector being fed by lubricating oil by means of a pump which removes the lubricant from a storage tank; suitable means for analyzing the solid and gases contained in the exhaust gases produced by the combustion in the engine.

14. The apparatus of claim 13, in which the injector, the head of the metering pump, the tank-pump, and pump-injector connection lines are maintained at constant temperature.

* * * * *